United States Patent [19]
Kent et al.

[11] 3,989,382
[45] Nov. 2, 1976

[54] PLATELET AGGREGATION MONITORING DEVICE

[75] Inventors: Frederick M. Kent, Warrington; Michael Sokol, Abington, both of Pa.

[73] Assignee: Bio-Data Corporation, Willow Grove, Pa.

[22] Filed: Jan. 22, 1975

[21] Appl. No.: 542,997

[52] U.S. Cl. ............................... 356/39; 23/230 B; 356/206
[51] Int. Cl.² .................. G01N 33/16; G01N 21/14
[58] Field of Search ............. 356/39, 197, 206, 208, 356/222, 226, 224, 229–230, 40–42, 104; 250/209, 565, 575, 578; 324/115, 140; 23/230 B; 73/64.1

[56] References Cited
UNITED STATES PATENTS

| | | | |
|---|---|---|---|
| 3,089,382 | 5/1963 | Hecht et al. | 356/51 |
| 3,658,480 | 4/1972 | Kane et al. | 356/39 |
| 3,711,774 | 1/1973 | Bohler | 324/115 |
| 3,809,482 | 5/1974 | Aslund et al. | 356/205 |
| 3,861,877 | 1/1975 | Matharani et al. | 356/39 |
| 3,879,135 | 4/1975 | Egli et al. | 356/229 |

Primary Examiner—John K. Corbin
Assistant Examiner—Wm. H. Punter
Attorney, Agent, or Firm—Seidel, Gonda & Goldhammer

[57] ABSTRACT

A difference amplifier continuously generates a signal representing the difference between the optical densities of a platelet rich and a platelet poor sample of blood plasma. A variable gain amplifier multiplies the difference signal by a factor which is proportional to the initial difference signal. Electronic circuitry automatically determines the multiplying factor by comparing the initial difference signal to a predetermined magnitude. The multiplied difference signal is continuously recorded on a chart recorder and an optional filter circuit is provided for selectively filtering the difference signal.

13 Claims, 5 Drawing Figures

PLATELET AGGREGATION MONITORING DEVICE

DISCLOSURE

The present invention relates to a platelet aggregation monitoring device and more particularly to a device which monitors and records platelet aggregation by measuring the optical densities of a platelet rich and a platelet poor sample of blood plasma and continuously generating a signal representing the difference between the two measured optical densities.

The blood platelet plays a unique roll in the maintenance of normal hemostasis and in the initiation of clot formation. Briefly, following injury to a blood vessel wall, the bruised vessel has exposed connective tissue and platelets which are cells found in the blood adhere to this tissue. This activity is known as platelet adhesion.

Once the platelets stick to exposed tissue, they then adhere to each other. The adhesion of platelets to each other, as distinct from their adhesion to foreign surfaces, is known as platelet aggregation. The initiation of the platelet aggregation occurs as a result of the exposed collagen in the surface of the blood vessel. As the platelets aggregate, they release adenosine diphosphate (ADP) which is found inside the platelets. The released ADP, then further causes the platelets to aggregate. Thus, platelet aggregation is actually a two-phased phenomena.

Methods of studying platelet aggregation in vitro have been known for some time. In the most frequently used method, platelet aggregation is recorded as the increase in light transmission which occurs when platelet aggregates form in a stirred platelet rich plasma. Platelet rich plasma (PRP) is turbid due to the presence of platelets in suspension. When the platelets aggregate, the turbidity decreases. A light beam is directed through the PRP and the percent transmission or optical density is recorded on a reader such as a chart recorder. The platelet aggregation is initiated by the addition of a reagent such as ADP. With normal platelets, two waves of aggregation are usually obtained. The first wave is due to the direct affect of the reagent and the second wave is the result of the ADP released from the platelets.

Platelet aggregation monitoring devices which carry out the above-described method are also known in the art. However, these prior art devices all suffer from the same basic defects. Their sensitivity is either fixed or manually adjustable and they, therefore, cannot automatically compensate for the differences in optical densities between plasma samples from different patients. Additionally, these devices use platelet poor plasma only as an initial reference and do not continuously monitor the difference between platelet rich and platelet poor specimens. This decreases the accuracy of the device and increases the time required for instrument set-up and standardization.

When making platelet aggregation measurements, one is not primarily concerned with the number of platelets in the sample but rather the concern is with the manner in which the platelets aggregate. The number of platelets, however, affects the optical density of the sample. Furthermore, the optical density in a plasma sample from one patient may be substantially different from a similar sample taken from a second patient even though the number of platelets may be the same. This is caused by a plurality of factors including bilirubin and lipemia in the plasma and set-up or adjustment error on the part of the operator.

Thus, prior art devices having a manually adjusted sensitivity may be capable of monitoring platelet aggregation activity in some samples but incapable of accurately monitoring platelet aggregation activity in other samples. In addition, they require a substantial amount of set-up time since the baseline must be adjusted prior to each test if full scale deflection is desired. Furthermore, the results of measurements made in prior art devices may be inaccurate as a result of those substances previously described and adjustment errors that can be present. Thus, it is the primary purpose of the present invention to provide a platelet aggregation monitoring device which automatically adjusts its sensitivity for full scale deflection for each sample being measured and which eliminates operator errors and errors which may be caused by other substances in the samples.

The invention accomplishes this by providing a difference amplifier which continuously generates a signal representing the difference between the optical densities of a platelet rich and a platelet poor sample of blood plasma. A variable gain amplifier multiplies the difference signal by a factor which is proportional to the initial difference signal. Electronic circuitry automatically determines the multiplying factor by comparing the initial difference signal to a predetermined magnitude. A chart recorder continuously records the multiplied difference signal.

For the purpose of illustrating the invention, there is shown in the drawings a form which is presently preferred; it being understood, however, that this invention is not limited to the precise arrangements and instrumentalities shown.

Figure 1:
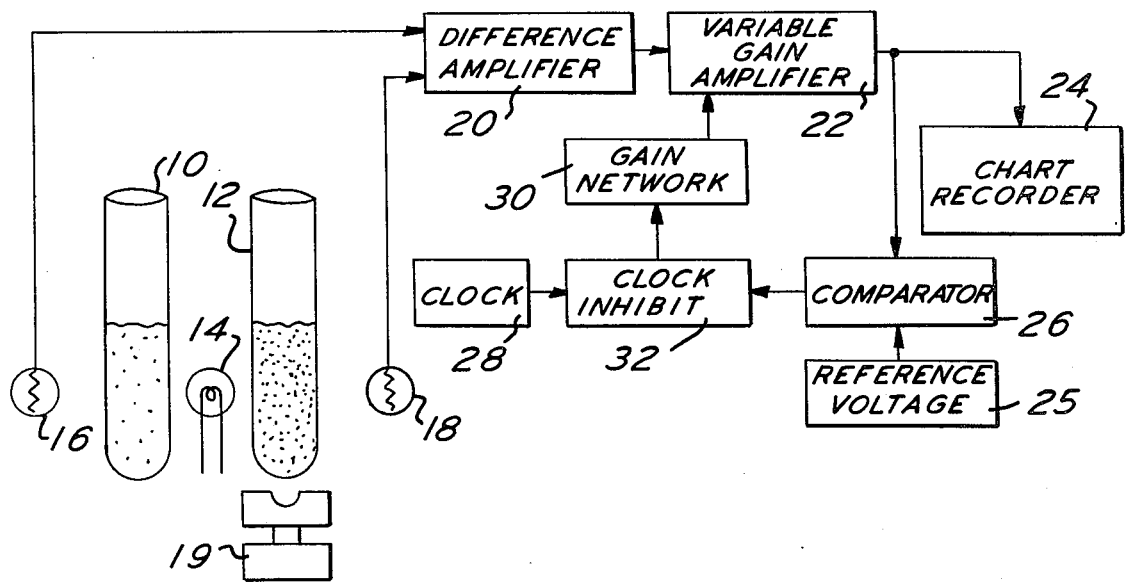
FIG. 1 is a block diagram of a preferred means for carrying out the present invention.

Referring now to the drawings in detail, there is shown in FIG. 1 a block diagram of a circuit for carrying out the present invention. As shown, test tubes 10 and 12 are positioned between a common light source 14 and photosensitive means such as photo-resistors 16 and 18, respectively. Test tube 10 contains a platelet poor plasma (PPP) sample and test tube 12 contains a platelet rich plasma (PRP) sample to which an aggregating agent such as ADP is to be added. These samples are prepared in a manner well known in the art. The contents of test tube 12 are continuously mixed by magnetic stirrer 19.

The output signals from photo-resistors 16 and 18, which signals represent the optical densities of the PPP and PRP samples respectively, are fed to the inputs of difference amplifier 20. The output of difference amplifier 20, therefore, represents the difference in the optical densities of the PPP and PRP samples. Since only the difference in the optical densities of the PPP and PRP samples is utilized, factors such as bilirubin and lipemia or the like in the samples which may affect the optical density are eliminated. This difference signal is then amplified by variable gain amplifier 22 and is thereafter recorded on chart recorder 24.

Figure 2:
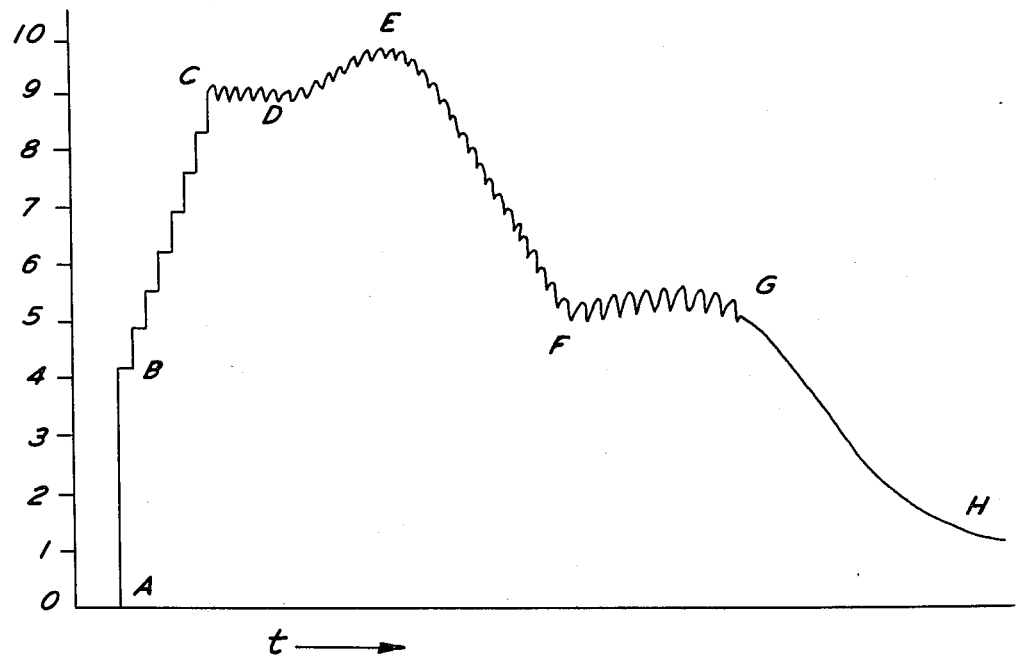
FIG. 2 is a graph illustrating a typical electrical output generated by the circuit shown in FIG. 1.

According to the principles of the present invention, the PPP sample is considered to be the zero reference and a constant difference is established on the chart recorder 24 between PPP and PRP. This constant desired difference is preferably at a point near full scale on the chart recorder 24. For example, as shown in FIG. 2, the constant difference represents nine major divisions on the chart. This corresponds to a voltage at the output of amplifier 22 of 10 volts. The tenth major division which represents full scale on the chart recorder 24 is not utilized since as a result of platelet swelling and oscillations caused by the agitation of the PRP sample the optical density of the PRP sample may increase slightly before it begins to decrease. This increase is shown in FIG. 2 at point E. Thus, if the tenth major division on the chart were chosen to represent the desired constant difference then the optical density increase shown at point E would not appear.

Referring again to FIG. 1, the constant difference is established by comparing the output of variable gain amplifier 22 to a fixed reference voltage 25 by comparator circuit 26. When the platelet aggregation monitoring device is initially started, the gain of the variable gain amplifier 22 begins to increase step wise. Each step increase is caused by a pulse from clock 28 entering gain network circuit 30. Eventually, the gain of variable gain amplifier 22 increases sufficiently so that its output is equal to the reference voltage 25 which as stated above is approximately 10 volts corresponding to nine major divisions on the chart of chart recorder 24. When this favorable comparison is sensed by comparator circuit 26, clock inhibitor circuit 32 prevents further clock pulses from clock 28 from passing to the gain network circuit 30. Thereafter, for the remainder of the test the gain of variable gain amplifier 22 remains constant.

Thus, it can be seen that the above-described circuit automatically provides a continuous differential comparison of the optical densities of the PRP and PPP samples thereby reducing the time required for instrument set-up and standardization. In addition, the circuit automatically standardizes the chart recorder for full scale deflection thereby eliminating the need for manual adjustment and readjustment of the chart recorder baseline.

Figure 3:
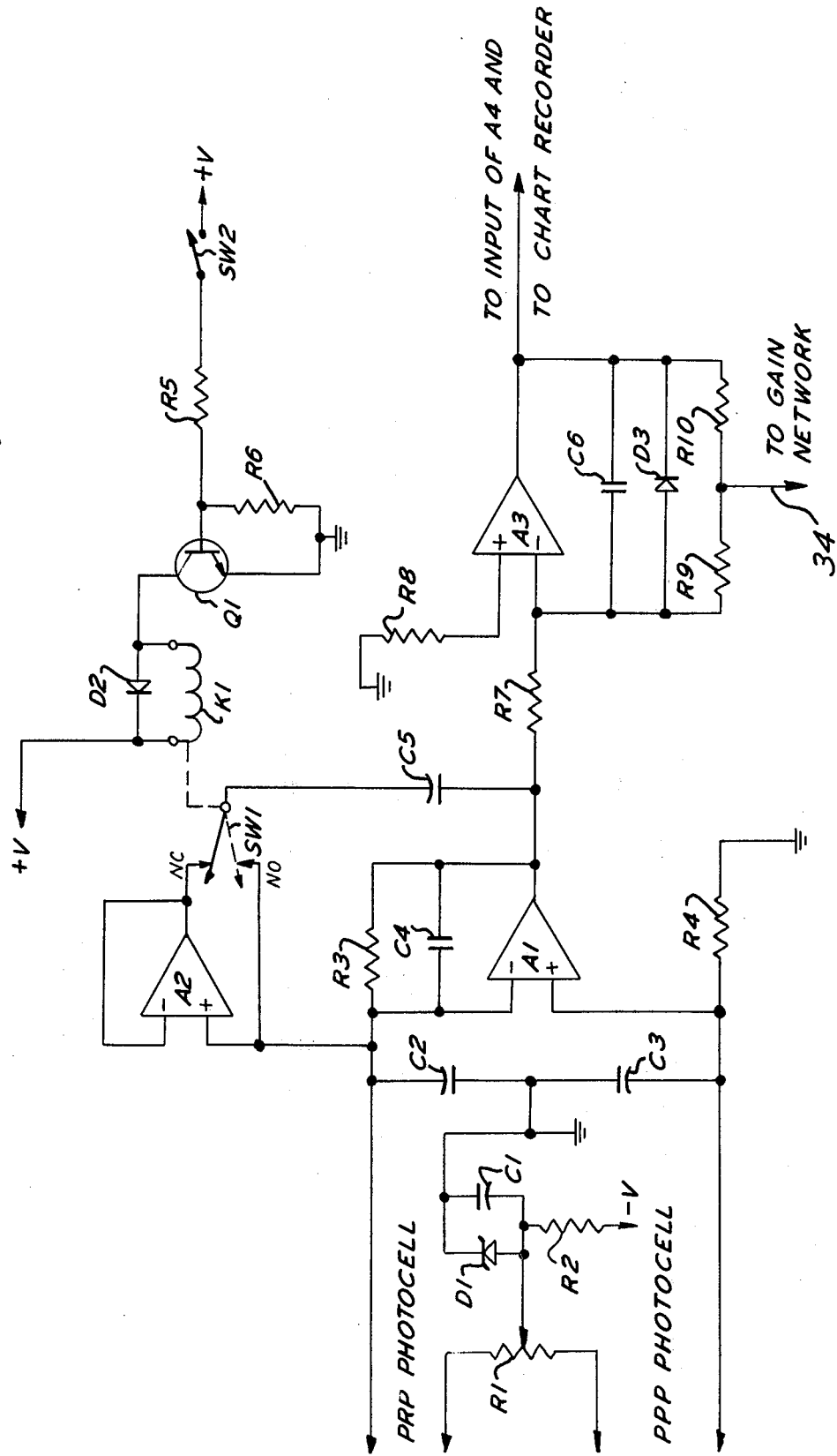
FIG. 3 is a schematic diagram of a preferred form of the difference and variable gain amplifiers shown in FIG. 1.

FIG. 2 represents the output of variable gain amplifier 22 as recorded on chart recorder 24. Point A on the curve represents zero optical difference which means that the difference in the optical density between the PPP sample and PRP sample is zero. Before any tests are run in the device, the light system and difference amplifier circuit 20 can be calibrated by replacing test tubes 10 and 12 with blank test tubes and adjusting the several components until the output of variable gain amplifier 22 is zero. As shown in FIG. 3, a variable resistor network R1 is provided for this purpose. Point B on the graph shown in FIG. 2 represents the initial difference in the optical densities between the PPP and PRP samples. Since the difference in the optical densities is not equal to the selected value represented by nine divisions on the chart, the gain of the variable gain amplifier 22 is automatically increased in a step wise progression as described above until the gain of the amplifier 22 is such that the needle of the chart recorder 24 is at the ninth division on the graph. This is represented by letter C in FIG. 2. At point D on the graph the ADP or other aggregating agent is added to the PRP sample and the remaining parts of the graph represent the difference in the optical densities between the PPP and PRP samples as the platelets aggregate in the PRP sample. As described above, after the addition of the aggregating reagent at point D, the platelets may swell causing an increase in density as shown at point E. It can then be seen that there are two waves of aggregation. The first is between points E and F and is caused by the aggregating reagent. The second wave can be seen between points G and H and is caused by intrinsic ADP release by the platelets themselves as they aggregate. The graph between points F and G represents a cessation of aggregation and in some instances may show disaggregation prior to intrinsic ADP release if it occurs.

FIG. 3 is a schematic diagram showing a preferred form of the difference amplifier and variable gain amplifier circuits shown in FIG. 1. As seen in FIG. 3, the difference amplifier is essentially an amplifier A1 having its inverting input connected to one side of the photo-resistor cell associated with the platelet rich plasma sample and its non-inverting input connected to one side of the photo-resistive cell associated with the platelet poor plasma sample. The other side of each of the two photo-resistive cells are connected to opposite ends of a poteniometer R1. The wiper arm of the potentiometer R1 is connected to one end of a parallel connected Zener diode D1 and capacitor C1 and to resistor R2. The other side of the parallel combination of Zener diode D1 and capacitor C1 is connected to ground and resistor R2 is connected to a negative voltage source. Potentiometer R1 serves as a fine adjust balance for initially calibrating the device.

Also connected to each of the inputs of amplifier A1 are capacitors C2 and C3. The other sides of capacitors C2 and C3 are connected to ground. In addition, the non-inverting input of amplifier A1 is connected to ground through resistor R4. Feedback resistor R3 and capacitor C4 are connected between the output of amplifier A1 and the inverting input.

The difference amplifier circuit just described, takes the photo-resistive cell outputs and provides an output signal which represents only the difference between the two inputs, the PPP input being referenced to ground.

As stated above, the difference signal represents the difference in the optical densities between the PRP and PPP samples and includes oscillations which are caused by the fact that the PRP sample is constantly being stirred. If these oscillations become too great, visual analyses of the output curve to determine the rate of aggregation on the chart of chart recorder 24 becomes very difficult. These oscillations are shown between points C and G in FIG. 2. Accordingly, the difference amplifier circuit of the present invention is provided with an optional filter which may selectively be placed into the feedback leg of the amplifier.

The filter is comprised essentially of a large capacitor C5 which may, when desired, be switched into the feedback leg of amplifier A1. Since it is desired to prevent the filter capacitor C5 from causing any significant shifting in the output signal of amplifier A1 when the filter is switched into the circuit, a buffer amplifier A2 is used to maintain the capacitor charge voltage at the proper level. Buffer amplifier A2 is connected as a non-inverting unity gain amplifier, which has a very high input impedance. When switch SW1 is in the position shown by the solid line in FIG. 3, capacitor C5 is effectively not in the feedback circuit since it has approximately 10 meg ohms in series with it. However, buffer amplifier A2 functions as a very low impedance voltage source and charges capacitor C5 so that when capacitor C5 is switched into the feedback path of amplifier A1, there is little or no effect on the average D.C. output of amplifier A1.

Filter capacitor C5 is switched into the feedback path of amplifier A1 when switch SW1 is in the position shown by the broken lines in FIG. 3. Switch SW1 is part of relay K1. One side of the coil of relay K1 is connected to a positive voltage source and the other side of the coil is connected to the collector of transistor Q1. A diode D2 is also connected across the coil of relay K1. The emitter of transistor Q1 is connected directly to ground. One side of resistors R5 and R6 are connected to the base of transistor Q1. The other side of resistor R6 is connected to ground and resistor R5 is connected to a positive voltage source through switch SW2. Thus, when it is desired to switch filter capacitor C5 into the feedback loop of amplifier A1, switch SW2 is closed thereby causing transistor Q1 to conduct, energizing relay K1 and closing switch SW1. As shown in FIG. 2, the filter was switched into the operative position at point G.

The output of amplifier A1 is fed through input resistor R7 to the inverting input of amplifier A3. The non-inverting input of amplifier A3 is connected to ground through resistor R8. Connected between the output of amplifier A3 and the inverting input are capacitor C6, diode D3 and series resistors R9 and R10. The conductor 34 is connected to the junction of resistors R9 and R10 and leads to the gain network circuit shown in FIG. 4. As will be described more fully below, the gain network circuit functions to change the resistance between conductor 34 and ground to thereby control the gain of amplifier A3. This arrangement of feedback resistors R9, R10 and the resistance in the leg connected to conductor 34 is known in the art as a Tee network. The output of amplifier A3 is connected to a chart recorder and also to the input of the comparator circuit described below.

Figure 4:
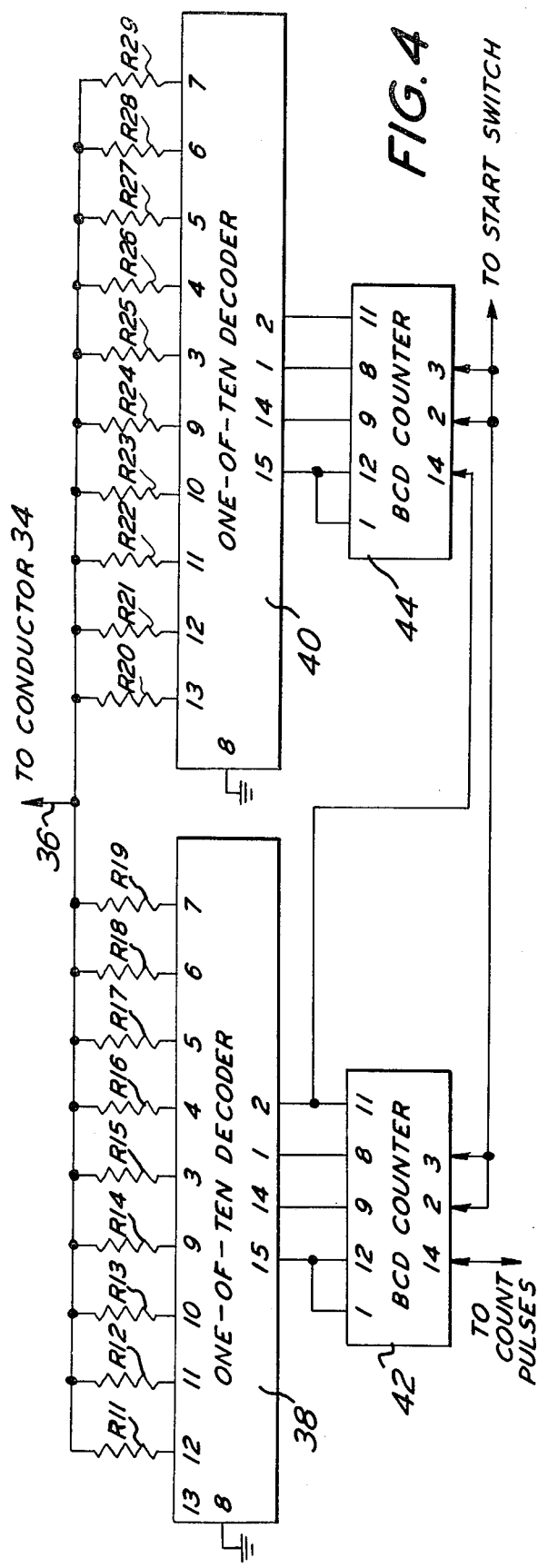
FIG. 4 is a schematic diagram of a preferred form of the gain network circuit shown in FIG. 1.

FIG. 4 is a schematic diagram of the gain network circuit 30 shown in FIG. 1 and is used to control the gain of the variable gain amplifier A3. The circuit is comprised essentially of nine "fine adjust" resistors R11-R19 and ten "coarse adjust" resistors R20-R29. One side of each of the resistors R11-R29 are connected together and to conductor 36 which in turn is connected to conductor 34 at the junction of amplifier A3 feedback resistors R9 and R10. The other side of each of the resistors R11-R19 is connected respectively to a different one of the last nine of the ten outputs of the one-of-ten decoder 38. The other side of each of the resistors R20-R29 is connected to a different one of the ten outputs of one-of-ten decoder 40. By way of example and not limitation, one-of-ten decoders 38 and 40 may be Fairchild 9302 decoders or equivalent circuits. The inputs of decoder 38 are connected to the outputs of BCD counter 42 and the inputs of decoder 40 are connected to the outputs of BCD counter 44. In addition, the last output at pin 11 of BCD counter 42 is connected to the input 14 of BCD counter 44. Also by way of example and not limitation, BCD counters 42 and 44 may be Fairchild 7490 decade counters or equivalent circuits.

The circuit shown in FIG. 4 functions as follows. Initially the outputs at pins 13 of decoders 38 and 40 are low and the remaining outputs are high. Accordingly, only resistor R20 is connected to ground and therefore affects the gain of amplifier A3. When the start switch (not shown) is depressed, reset terminals 2 and 3 of BCD counters 42 and 44 are opened and the clock pulses received at input pin 14 of BCD counter 42 cause counter 42 to begin counting. As counter 42 counts, the resistors R11-R29 are switched into the circuit according to the following sequence. R11 in; R11 out, R12 in; R12 out, R13 in; R13 out, R14 in, etc. Each time resistor R19 is switched out of the circuit the pulse at output pin 11 of counter 42 causes counter 44 and decoder 40 to advance resistors R20-R29 by one. This progression continues as long as the clock pulses are received at input pin 14 to BCD counter 42.

In the preferred embodiment, the values of the resistors R11-R29 have been selected so that as each fine resistor R11-R19 is switched in parallel with a coarse resistor R20-R29 the gain of amplifier A3 is incrementally increased. The step wise increase in gain is shown on the graph in FIG. 2 between points B and C. This particular embodiment incorporates 99 steps as shown; however, it is obvious that additional decades can be added for greater range or finer control.

Figure 5:
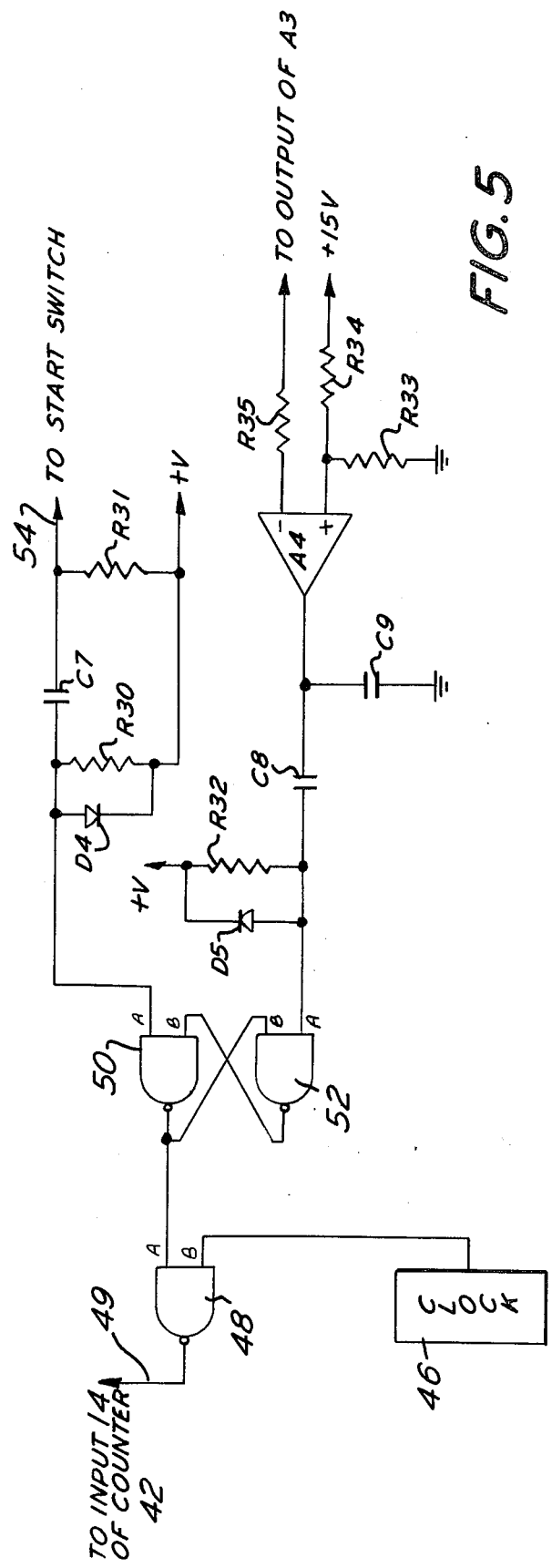
FIG. 5 is a schematic diagram of a preferred form of the comparator and clock inhibit circuits shown in FIG. 1.

The clock pulses which control the switching of resistors R11-R29 and thereby the gain of amplifier A3 are controlled by the circuit shown in FIG. 5. The clock pulses are derived from clock 46 and are delivered to input 14 of counter 42 through NAND gate 48 and conductor 50. Normally, however, gate 48 is inhibited thereby preventing clock pulses from clock 46 from reaching the input to counter 42. Gate 48 is selectively set and reset by NAND gates 50 and 52.

The output of NAND gate 50 is connected to input A of gate 48 and to input B of NAND gate 52. Similarly, the output of NAND gate 52 is connected to input B of NAND gate 50. Input A to NAND gate 50 is connected to the junction of diode D4, resistor R30 and capacitor C7. The other sides of diode D4 and resistor R30 are connected together, to resistor R31 and to a positive voltage source. Resistor R31, in turn, is connected to the other side of capacitor C7 and to conductor 54. Conductor 54 is connected to a start switch, (not shown).

Similarly, input A of NAND gate 52 is connected to the junction of diode D5, resistor R32 and capacitor C8. The other side of diode D5 and resistor R32 are connected to a positive voltage source. The other side of capacitor C8 is connected to the output of comparator amplifier A4 and to one side of capacitor C9 which in turn is connected to ground. The inverting input of comparator amplifier A4 is connected to the output of variable gain amplifier A3 through input resistor R35. The non-inverting input of comparator amplifier A4 is connected to a positive voltage source by a divider network comprised of resistor R34 and resistor R33. The values of resistors R33 and R34 and this positive voltage source are selected so that the voltage at the non-inverting input to comparator amplifier A4 is approximately 10 volts. As stated above, this value represents nine major divisions on the chart of the chart recorder 24.

The circuit shown in FIG. 5 functions as follows. Before the test is started, input A to gate 48 is low thereby preventing the clock pulses from clock 46 from passing through gate 48 to BCD counter 42. In addition, inputs A to gates 50 and 52 are maintained high by the positive voltage sources connected to resistors R30 and R32, respectively. When the start switch is depressed, capacitor C7 discharges and a momentary low pulse is generated at input A to gate 50. This causes the output of gate 50 to go high thereby allowing clock pulses from clock 46 to pass through gate 48 to counter 42. During this time, the gain of variable gain amplifier A3 increases in a step wise manner as described above. The gain continues to increase until the output of amplifier A3 reaches ten volts which represents the ninth major division on the chart of the chart recorder 24. This is determined by comparator amplifier A4 which has as its inputs the output of variable gain amplifier A3 and a fixed reference voltage of 10 volts. When a favorable comparison is determined, the output of amplifier A4 which is normally high goes low, discharging capacitor C8 which provides a momentary negative pulse at input A of NAND gate 52. This in turn causes the output of NAND gate 52 to go high thereby creating a low at the output of NAND gate 50 which in turn inhibits gate 48 from passing any further clock pulses from clock 46 to counter 42. Accordingly, further increase in the gain of variable amplifier A3 is prevented. The gain of amplifier A3, therefore, remains constant during the platelet aggregation test on the plasma samples and remains constant until the circuitry is reset.

The values of the various components used in the circuits of FIGS. 3, 4 and 5 are shown in the Table below. It should be noted, however, that these values merely represent the preferred embodiment of the invention and that various other components and circuit arrangements could obviously be substituted without departing from the spirit and scope of the present invention.

TABLE

| R1 | = 5K | R13 | = 20.5K | R25 | = 1.13K |
|---|---|---|---|---|---|
| R2 | = 2.2K | R14 | = 15.4K | R26 | = .953K |
| R3 | = 39K | R15 | = 12.4K | R27 | = .825K |
| R4 | = 39K | R16 | = 10.2K | R28 | = .732K |
| R5 | = 1K | R17 | = 8.87K | R29 | = .649K |
| R6 | = 4.7K | R18 | = 7.68K | R30 | = 10K |
| R7 | = 33K | R19 | = 6.98K | R31 | = .27K |
| R8 | = 10K | R20 | = 12.4K | R32 | = 10K |
| R9 | = 33K | R21 | = 4.12K | R33 | = 10K |
| R10 | = 33K | R22 | = 2.49K | R34 | = 5.1K |
| R11 | = 61.9K | R23 | = 1.78K | R35 | = 10K |
| R12 | = 30.9K | R24 | = 1.37K | | |
| C1 | = 6 ufd | C4 | = .47 ufd | C7 | = .47 ufd |
| C2 | = 22ufd | C5 | = 100 ufd | C8 | = .47 ufd |
| C3 | = 22 ufd | C6 | = .001 ufd | C9 | = .1 ufd |
| D1 | = 1N5233 | | D4 | = 1N4454 | |
| D2 | = 1N4454 | | D5 | = 1N4454 | |
| D3 | = 1N4454 | | Q1 | = 2N3646 | |

The present invention may be embodied in other specific forms without departing from the spirit or essential attributes thereof and, accordingly, reference should be made to the appended claims, rather than to the foregoing specification as indicating the scope of the invention.

We claim:

1. A platelet aggregation monitoring device comprising:
    means for continuously generating a signal representing the difference in the optical densities of a platelet rich plasma sample and a platelet poor plasma sample;
    means for multiplying said signal by a variable factor;
    means for automatically adjusting said factor such that said multiplied signal is initially equal to a preselected standard value, whereby the sensitivity of the device is automatically adjusted;
    and means for maintaining said factor constant once it has been adjusted to the point that said multiplied signal is equal to said preselected standard value.

2. A platelet aggregation monitoring device as claimed in claim 1 further including means for recording the output of said multiplying means.

3. A platelet aggregation monitoring device as claimed in claim 1 wherein said multiplying means comprises a variable gain amplifier and a means for varying the gain of said amplifier.

4. A platelet aggregation monitoring device as claimed in claim 3 wherein said means for varying said gain includes variable resistance means.

5. A platelet aggregation monitoring device as claimed in claim 4 wherein said variable gain amplifier includes a feedback path and wherein said variable resistance means includes a plurality of resistors and further including means for selectively connecting said resistors to said feedback path.

6. A platelet aggregation monitoring device as claimed in claim 1 wherein said adjusting means includes a comparator means and wherein said maintaining means includes means responsive to said comparator means for preventing further adjustment of said factor once said multiplied signal is equal to said preselected standard value.

7. A platelet aggregation monitoring device as claimed in claim 1 wherein said means for adjusting said factor increases said factor in a step wise manner.

8. A platelet aggregation monitoring device as claimed in claim 1 wherein said means for continuously generating said signal comprises a difference amplifier, said difference amplifier having a first input connected to a photosensitive means associated with said platelet rich sample and a second input connected to a photosensitive means associated with said platelet poor sample.

9. A platelet aggregation monitoring device as claimed in claim 8 further including a filter means and means for selectively placing said filter means between the output of said difference amplifier and said first input.

10. A platelet aggregation monitoring device as claimed in claim 9 wherein said filter means includes a capacitor and further including means for charging said capacitor with the voltage received at said first input when said filter means is not placed between said output and said first input of said difference amplifier.

11. A platelet aggregation monitoring device comprising:
    means for generating a first signal representing the optical density of a platelet rich plasma sample;
    means for generating a second signal representing the optical density of a platelet poor plasma sample;
    means for generating a third signal proportional to the difference between said first and said second signal;
    means for multiplying said third signal by a variable factor;
    means for comparing said multiplied third signal to a preselected standard value;

means for automatically varying said factor until said comparator means senses that said multiplied third signal is equal to said standard value;

and means for automatically maintaining said factor constant after it has been varied to the point that said multiplied third signal is equal to said standard value.

12. A platelet aggregation monitoring device as claimed in claim 11 further including means for recording the output of said multiplying means.

13. A platelet aggregation monitoring device as claimed in claim 11 wherein said means for varying said factor increases said factor in a stepwise manner.

* * * * *